United States Patent
Richter et al.

(10) Patent No.: US 9,599,555 B2
(45) Date of Patent: Mar. 21, 2017

(54) DOPING PROFILE MEASUREMENT USING TERAHERTZ TIME DOMAIN SPECTROSCOPY (THZ-TDS)

(71) Applicants: Christiaan Richter, Rochester, NY (US); Chih-Yu Jen, Rochester, NY (US)

(72) Inventors: Christiaan Richter, Rochester, NY (US); Chih-Yu Jen, Rochester, NY (US)

(73) Assignee: Rochester Institute of Technology, Rochester, NY (US)

(*) Notice: Subject to any disclaimer, the term of this patent is extended or adjusted under 35 U.S.C. 154(b) by 0 days.

(21) Appl. No.: 14/941,099

(22) Filed: Nov. 13, 2015

(65) Prior Publication Data

US 2016/0139044 A1    May 19, 2016

Related U.S. Application Data

(60) Provisional application No. 62/079,262, filed on Nov. 13, 2014.

(51) Int. Cl.
*G01N 21/3586* (2014.01)
*G01N 33/00* (2006.01)

(52) U.S. Cl.
CPC ......... *G01N 21/3586* (2013.01); *G01N 33/00* (2013.01); *G01N 2033/0095* (2013.01)

(58) Field of Classification Search
CPC .... G01N 21/3586; G01N 21/55; G01N 21/59; G01N 33/00
See application file for complete search history.

(56) References Cited

U.S. PATENT DOCUMENTS

| | | | |
|---|---|---|---|
| 7,439,511 B2 | 10/2008 | Demers | |
| 7,459,687 B2 | 12/2008 | Federici et al. | |
| 8,344,324 B2 | 1/2013 | Kasai et al. | |
| 2009/0206263 A1* | 8/2009 | Rahman | G01J 3/02 250/341.1 |

FOREIGN PATENT DOCUMENTS

| | | | |
|---|---|---|---|
| EP | 2233914 A1 | 9/2010 | |
| JP | EP2233914 | * 11/2008 | G01N 21/35 |

(Continued)

OTHER PUBLICATIONS

Hunsche, S., Koch, M., Brener, I., & Nuss, M. C. (1998). THz near-field imaging. Optics communications, 150(1), 22-26.

(Continued)

*Primary Examiner* — David Porta
*Assistant Examiner* — Faye Boosalis
(74) *Attorney, Agent, or Firm* — Joseph N. Noto; Bond, Schoeneck & King PLLC

(57) ABSTRACT

A system and method for determining a doping profile of a sample includes a generator and at least one detector of terahertz light of multiple frequencies, configured to operate in a transmission and/or reflection mode; a materials refractive index library; and an inverse algorithm that can match simulated spectra using a trial doping profile and the materials library with the measured spectra from a sample, and map out or measure an activated doping profile into, or a free carrier distribution into, the interior of the sample.

21 Claims, 6 Drawing Sheets

(56) References Cited

FOREIGN PATENT DOCUMENTS

| WO | WO0050859 | 8/2000 |
| WO | WO0075641 A1 | 12/2000 |
| WO | WO0165238 A1 | 9/2001 |
| WO | WO03042670 A1 | 5/2003 |
| WO | WO2008122597 A1 | 10/2008 |

OTHER PUBLICATIONS

Boosalis, A., Hofmann, T., Šik, J., & Schubert, M. (2011). Free-charge carrier profile of iso-and aniso-type Si homojunctions determined by terahertz and mid-infrared ellipsometry. Thin Solid Films, 519(9), 2604-2607.

Hofmann, T., Herzinger, C.M., Boosalis, A., Tiwald, T.E., Woollam, J.A., Schubert, J. (2010). Variable-wavelength frequency-domain terahertz ellipsometry. Review of Scientific Instruments. 81, retrieved from http://dx.doi.org/10.1063/1.3297902.

Ulbricht, R., Hendry, E., Shan, J., Heinz, T.F., Bonn, M., Carrier dynamics in semiconductors studied with time-resolved terahertz spectroscopy. Rev. Mod. Phys. 83, 543 (2011) Published Jun. 3, 2011.

Fekete, L., Kužel, P., Němec, H., Kadlec, F., Dejneka, A., Stuchlík, J., Fejfar, A. Ultrafast carrier dynamics in microcrystalline silicon probed by time-resolved terahertz spectroscopy. Phys. Rev. B 79, 115306 (2009)—Published Mar. 10, 2009.

Hofmann, Tino; Herzinger, C. M.; Tiwald, T. E.; Woollam, J. A.; and Schubert, Mathias, "Hole diffusion profile in a p-p+ silicon homojunction determined by terahertz and midinfrared spectroscopic ellipsometry" (2009). Faculty Publications from Nebraska Center for Materials and Nanoscience. Paper 99. Retreived from http://digitalcommons.unl.edu/cmrafacpub/99.

* cited by examiner

DOPING PROFILE MEASUREMENT USING TERAHERTZ TIME DOMAIN SPECTROSCOPY (THZ-TDS)

CROSS REFERENCE

This application claims the benefit of the filing date of U.S. Provisional Patent Application Ser. No. 62/079,262, filed Nov. 13, 2014, which is hereby incorporated by reference in its entirety.

FIELD

The present disclosure relates to a system and method for determining a doping profile of a sample using terahertz frequency radiation.

BACKGROUND

Around 1975 David Auston discovered the so-called "Auston switch" at Bell Labs, basically the use of ultrashort laser pulses to generate an electrical or current pulse in a material that in turn, so it was discovered, radiate short broadband pulses of terahertz light. This discovery, after contributions by others in particular Dan Grischowsky and Allan Cheville (IBM Watson Research Center, around 1986) was developed into the modern laboratory technique called Terahertz Time-Domain Spectroscopy (THz-TDS). Since around 1990 this technique has been used mostly in academic laboratories for scientific research. In more recent years, starting around 2005, advances in Fiber laser systems led to a new generation of robust fiber based pulsed THz-TDS systems that are lower cost and can be deployed in the field—that is in industry, specifically in for example industrial research laboratories, medical centers or even on the manufacturing floor.

However, even though in many industries there is an expectation that there could be useful application for this technology there is at the same time in most industries as yet (2015) no proven useful applications. In the case of the semiconductor industry in particular terahertz light is expected to have great utility. Only in the terahertz region of the electromagnetic spectrum can one probe free carriers (electrons and holes) and measure the free electron spectrum directly within semiconductors, nanomaterials and thin metallic layers. Terahertz light can penetrate into and transmit through most materials, excluding metals. Since free carriers are critical to most semiconductor applications including all electronics, touch screens, LED's, batteries, power electronics and solar cells there is many sectors terahertz technology may enable highly desirable measurements.

Doping profiles play a critical role in many technologies, an important example of which is diodes. Diodes are a critical component in virtually all electronics and solar cells. The major disadvantages of the current approach are that it fails to enable the measurement of a junction doping profile using a fast, non-contact non-destructive method. The existing technologies for doping profile measurement are destructive, slow and for the most part significantly more expensive.

Currently SIMS and ECV are the techniques relied on to measure semiconductor device doping profiles. SIMS measures the chemical profile of dopants as opposed to the true doping profile (it cannot distinguish between dopant atoms at dopant sites and not at dopant sites in a crystal) and ECV measures the surface electric doping profile after etching. The shared drawbacks from these existing widely used techniques are that they are destructive measurements and have long measurement time. The art lacks an optical non-contact non-destructive measurement technique that can provide measurement of doping profiles fast and at lower cost and be incorporated into the production line for inline process monitoring with either real time or close to real time feedback.

Secondary ion mass spectroscopy (SIMS) and electrochemical capacitance-voltage (ECV) measurements represent existing alternatives and their strengths and weaknesses include the following. SIMS: destructive, time consuming, need to handle pollution after the process. Furthermore, SIMS measures the chemical doping profile as opposed to the profile of activated dopants (or free electron distribution) as do the THz technique described here. ECV: destructive, time consuming, need to handle pollution after the process.

However, the raw terahertz data is simply electrical pulses and none of this raw data can easily and directly be translated into useful information in semiconductor research or manufacturing. What the art lacks is a system and method to configure terahertz measurements and process the resultant raw data to solve a longstanding problem in semiconductor research and manufacturing (see for example Davis, K., H. Seigneur, A. Rudack, and W. V. Schoenfeld, PVMC Tackles c-Si Metrology Challenges, U.S. Photovoltaic Manufacturing Consortium. 2012). The problem solved by the present invention is the ability to accurately, rapidly and non-destructively measure the activated doping profile within (below the surface into the material) semiconductor wafers. This is done significantly more cost effectively compared with the only standard existing approach, Secondary Ion Mass Spectroscopy that is completely destructive, slow, and very expensive and cannot measure the true activated doping profile but instead only the chemical doping profile.

SUMMARY

In accordance with one aspect of the present disclosure, there is provided a system for determining a doping profile of a sample including a generator of terahertz light of multiple frequencies; a first detector of terahertz light of multiple frequencies, wherein the generator and first detector are configured to operate in a transmission or reflection mode with respect to exposing a sample of unknown doping profile and an undoped reference sample to terahertz frequency radiation and detecting a measured spectra of terahertz frequency; a materials refractive index library including terahertz complex refractive index as a function of doping; and a processor including an inverse algorithm that can match simulated spectra using a trial doping profile and the materials library with the measured spectra from the sample, and map out or measure an activated doping profile into, or a free carrier distribution into, the interior of the sample.

In accordance with another aspect of the present disclosure, there is provided a method for determining a doping profile of a sample including providing a generator of terahertz light of multiple frequencies; providing a first detector of terahertz light of multiple frequencies, wherein the generator and first detector are configured to operate in a transmission or reflection mode; exposing a sample of unknown doping profile and an undoped reference sample to the terahertz frequency radiation and detecting a measured spectra of terahertz frequency; providing a materials refractive index library including terahertz complex refractive index as a function of doping; providing a processor including an inverse algorithm; and matching simulated spectra using a trial doping profile and the materials library with the measured spectra from the sample, to map out or measure the doping profile or chemical depth profile of the sample.

In accordance with another aspect of the present disclosure, there is provided a system for determining a doping profile of a sample including a generator of terahertz light of multiple frequencies; a first detector of terahertz light of multiple frequencies, wherein the generator and first detector are configured to operate in a transmission or reflection mode, or a first and second detector of terahertz light of multiple frequencies, wherein the generator, first detector and second detector are configured to operate in a transmission and reflection mode, with respect to exposing a sample of unknown doping profile and a doped reference sample having a known doping profile to terahertz frequency radiation and detecting a measured spectra of terahertz frequency; and a processor including an inverse algorithm that can determine the deviation of the doping profile or chemical depth profile of the sample of unknown doping profile from the reference sample of known doping profile.

DETAILED DESCRIPTION

A system and method is disclosed that can non-destructively, rapidly and accurately measure doping profiles (and free carrier distributions) within samples, e.g. wafers. The system and method combine the following components: 1) A way to configure any of the existing or future terahertz generators and detectors relative to wafers (samples) so as to transmit the terahertz light through the wafers and detect the terahertz light after transmission and then 2) A mathematical method or algorithm capable of analyzing the terahertz spectra thus obtained. The algorithm has the ability to extract from the raw data measured by the configuration in 1) the doping profiles or free carrier distribution below the surface into the bulk of the wafer with no contact or damage to the wafer. The physical embodiment of this method is a software algorithm or program. 3) The mathematical algorithm utilizes certain knowledge about the material to be measured. For example, if the sample is a p-type silicon wafer with an n-type doping profile then the algorithm needs to know the complex terahertz refractive index of silicon doped with the relevant n-type at the doping levels within the diode to be mapped. Hence, a third component of the system and the method described is a particular kind of data file herein referred to as the "materials library". The materials library contains information about the terahertz absorption and refractive index of the material in which the doping profiles are desired to be mapped. This information is needed at several doping concentrations that span the doping range to be encountered in the diodes or doping profiles to be mapped. 4) Disclosed is a method for generating material libraries for any semiconductor-dopant combination.

In summary, disclosed is a system and method that use existing or future broadband terahertz generation and detection technology and by combining and configuring this existing hardware with components (algorithm and materials library) achieve previously unimagined capability—specifically the ability to map or measure doping profiles with sub 10 nm resolution into the interior of semiconductor sample and wafers, and do this non-destructively, rapidly and cost-effectively.

Figure 1:
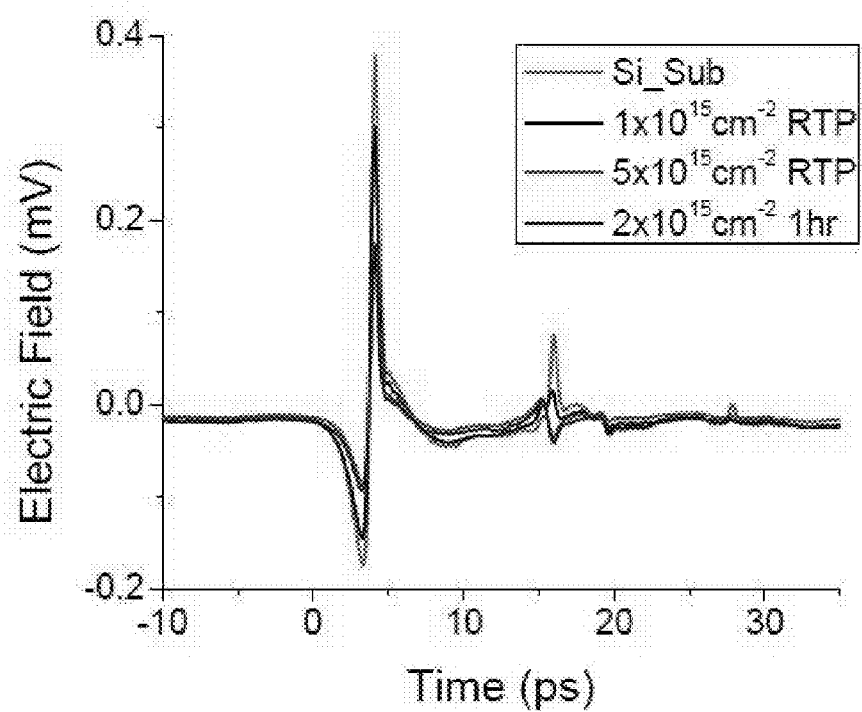
FIG. 1 shows raw data of a time domain THz (THz-TDS) measurement which is composed of the electrical pulse shapes of pulses of terahertz light measured after it was transmitted through various doped, or in one case an undoped, silicone wafers.

FIG. 1 is an example of time domain THz measurements from an undoped silicon wafer and three wafers with doping profiles (ion implantation dosages of phosphorous as indicated followed by either rapid thermal anneal or 1 h drive-in). Note the raw data is simply the electric field of short, ~1 ps peak width, pulses of terahertz light that was transmitted through the wafer or sample. However, the raw terahertz data is simply electrical pulses as shown in FIG. 1 which in itself, or just as measured, is of very limited utility. One can take the Fourier transform of these pulses to obtain a complex valued spectrum. However, previously none of this raw data could easily and directly be translated into useful information in semiconductor research or manufacturing.

Figures 2A, 2B:
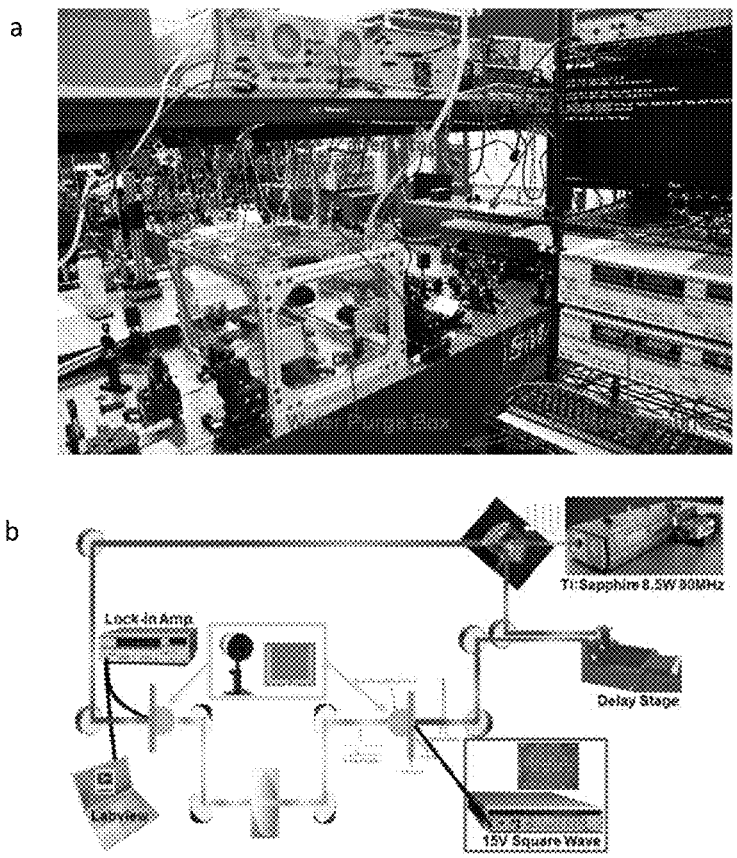
FIG. 2A shows a photo of a laboratory scale THz-TDS system and FIG. 2B shows a schematic of a laboratory scale THz-TDS system in accordance with an embodiment of the present invention.

FIGS. 2a & 2b show a photo and schematic of a laboratory scale THz-TDS system. The mapping system of this disclosure can include either standard laboratory systems as shown or known in the art to generate and detect terahertz, or any of the existing fiber laser based commercial terahertz generation or detection systems, or a frequency domain photomixing system, or any future method for generating and detecting multi-frequency terahertz radiation. The method can be implemented with a mapping system that can, for terahertz generation and detection, incorporate any one of these existing ways of generating and detecting terahertz. To the terahertz generation and detection components are added a way, for example GPIB cables or wireless, to feed the raw data into a computer, the computer is equipped with the reconstruction algorithm described below and the reconstruction algorithm in turn is supplied with a suitable materials library described below. The algorithm program or software can be executed by processors and computers known in the art for processing software or programs. This mapping system can then non-destructively predict from the raw data what the doping profile within the wafer is by enabling the implementation and execution the method for doping profile measurement and monitoring described here. There are several embodiments of the present disclosure that can be used to measure depth profiles in doping and concentration in samples, e.g., thin films, coatings and wafers.

In an embodiment, the present disclosure maps out doping profiles quickly, non-destructively and relatively cheaply by measuring THz spectra of a target using existing hardware;

creating an index library of known materials with known profiles; and applying a suitable inverse algorithm to the data collected.

An embodiment includes a set of methodologies that use terahertz radiation to monitor, measure, map and image doping profiles in thin films, wafers and coatings. 2D terahertz imaging technologies already exist. Typically they work quite simply by moving either the sample or the terahertz beam to sample different spots on a wafer. This invention describes a 3D imaging technique that can, in addition to sampling different locations on a wafer, map out depth profiles below the surface into the bulk of the wafer. The methodologies described here go beyond 2D imaging techniques by mapping out and resolving doping or chemical composition profiles normal to the sample or wafer surface.

The physics that our invention exploits is based on the fact that 1) free carrier absorption is the dominant optical feature in the terahertz part of the electromagnetic spectrum for virtually all commercially relevant semiconductors providing an un-obscured window for doping profile mapping, 2) free carrier absorption typically increases by orders of magnitude as a function of doping concentration providing high contrast for doping profile mapping and 3) the real and imaginary refractive index for these materials change significantly as a function of terahertz frequency and doping profile providing a way to reconstruct doping profiles using broadband terahertz data. The absorption spectrum of doped silicon from the microwave to the UV is shown below. Silicon is a good example, clearly having all three of the enabling characteristics described above. Thus, since THz sees electrons, the present disclosure is capable of determining the effective doping level as opposed to just the chemical doping level of a sample.

An embodiment includes a non-destructive transmission mode measurement or a reflection mode measurement with the use of one generator and one detector. This approach can utilize any coherent sufficiently broadband source (typically pulsed THz-TDS or CW photomixing) that can simultaneously measure the phase and/or amplitude (real and imaginary refractive index) of the material to be analyzed. The phase and/or amplitude of terahertz radiation of different frequencies that is transmitted through or reflected off the sample and an undoped reference wafer is measured. The doping profile of the sample is reconstructed from this data (by first dividing the sample frequency spectrum by the reference frequency spectrum) and then using the materials library and algorithms, as for example illustrated in FIG. 3. For lightly doped samples the transmission mode is relatively more accurate, and for highly doped samples the reflection mode with the sample measured from both ends (highly doped surface front and then highly doped surface at the back) is relatively more accurate.

A typical THz-TDS system as shown in FIG. 2A and schematically illustrated in FIG. 2B works as follows: A standard ultrafast laser is used to generate short pulses of light. The light is typically red light (around 800 nm) or sometimes in the NIR. The pulse length is typically 10 fs to 200 fs, the shorter the better (it will produce more terahertz frequencies). The beam of pulsed red light is split in two. One beam will be used to generate pulses of terahertz light. The second beam will be used to gate (switch "on" and "off") the terahertz detector. The generation beam is then used to generate a short pulse of terahertz light containing multiple frequencies. There currently are three widely used approaches for generation. The oldest is using a "photoconductive antenna" (also known as a PCA or Auston switch). Alternatives include using optical rectification in a suitable crystal like ZnTe or materials like the polymer DAST. A third option is using air plasma generation. Next, the terahertz radiation or pulse thus generated is collimated typically using silicon lenses and curved metallic mirrors (acting both as lenses and mirrors of terahertz light). Finally, in the embodiment the terahertz light is focused on the spot on the sample or wafer where the measurement is to be made. If it is a transmission measurement the sample is typically oriented relative to the terahertz beam path at 90° (normal incidence). The fraction of the terahertz beam that does not reflect from the front surface of the sample/wafer then propagates through the wafer including through the doping profile to be mapped. This pulse and multiple internal reflections of this pulse, then exit at the far side of the wafer. This radiation is then collected at the backside of the wafer, typical again by lenses and mirrors including curved metallic mirrors and/or silicon lenses. Finally the transmitted terahertz pulse shape is mapped out. This is typically done, either again by a second photoconductive antenna (used as a detector), or by free space electro-optic sampling. The detector laser beam is used to time the moment when the terahertz waveform is sampled. By repeating the experiment and changing the precise moment when the gating pulse arrives, the terahertz waveform can be measured on the required sub-picosecond time-scale.

For an embodiment where the measurement is done in reflection mode the light reflected from the front face of the sample/wafer is collected and detected instead. The measurement so far described and shown in FIG. 2 provides a pulse that looks like that shown in FIG. 1. This is referred to as the 'raw data'. Although this 'time domain' pulse was shaped by the doping profile through which it transmitted (or from which it reflected) there is no obvious way to tell from the time domain pulse exactly what shape the doping profile has. In fact there is no known example in the published literature or patent literature where anyone even suggested or proposed that this might be possible.

The method described here explains how this raw THz-TDS measurement can be used to non-destructively map out or measure with up to nanometer resolution the doping profile within samples and wafers. The system includes combining a measurement of multiple terahertz frequencies transmitted through or reflected from the sample with the method just described (or any other method with similar ability to measure the transmission or reflection of multiple terahertz frequencies), which is then combined with an algorithm and with a materials library to construct from the raw data the shape of the doping profile. The operating principles of the algorithm and the materials library are described in detail below.

An embodiment includes the non-destructive transmission mode and reflection mode measurements utilizing one generator and two detectors. This approach can utilize any coherent sufficiently broadband source (typically pulsed THz-TDS or CW photomixing) that can simultaneously measure the phase and amplitude (real and imaginary refractive index) of the material to be analyzed. The phase and amplitude of terahertz radiation of different frequencies that is focused on the sample and an undoped reference wafer and both the transmitted and reflected radiation are measured either simultaneously or successively. The doping profile is reconstructed from this data (by first dividing the sample frequency spectrum by the reference frequency spectrum) and then using the materials library and algorithm. Having both the transmitted and reflected spectra allows for the most accurate doping profile mapping over the largest doping density range. Ideally both the front end and back end reflection should be measured but practically just measurement of reflection form either just the undoped or back surface or just the doped or front surfaces can be used.

The measurement system configuration can be that as shown in FIG. 2B or described in detail for the embodiment above. A difference is that in this embodiment both the transmitted and reflected light are collected and measured using either two detectors (or one detector designed such that the arrival of the transmitted and reflected is pulses is at different times so that they can be resolved separately).

In this embodiment where the raw data is composed of two pulses as in FIG. 1, one transmitted through the wafer and one reflected from the front of the wafer the search algorithm (described in detail below) will simulate both the reflection and transmission and continue adjusting the 'guess' profile until both the simulated transmitted spectrum and the simulated reflected spectrum of the 'guess' profile is sufficiently close to the measured transmitted and reflected profile. What is sufficiently close will be measured with and determined by an error metric, as set forth with respect to the algorithm, that quantifies the match between both the transmitted and reflected spectra.

The embodiment that includes the measurement and matching of both the transmitted and reflected pulses has higher resolution and dynamic range and can also indicate if the alignment of the sample in the measurement does not agree with the model in the simulation (usually normal incidence) i.e., this configuration can detect misalignment of the measurement system.

An embodiment includes the destructive reflection and/or transmission mode measurement from one generator and one or two detectors with sample etching. This approach can utilize any coherent sufficiently broadband source (typically pulsed THz-TDS or CW photo-mixing) that can simultaneously measure the phase and amplitude (real and imaginary refractive index) of the material to be analyzed. Wet (electrolyte or chemical etching), dry (plasma etching) or CMP (chemical-mechanical polish) are used or incorporated in the measurement apparatus to etch the silicon or sample one layer at a time together with an undoped reference wafer with a pre-assigned etching amount per step. After every etching step the phase and amplitude of terahertz radiation of different frequencies is focused on the sample, the undoped reference wafer (and optionally also part of the sample wafer that was not etched) and either just the transmitted or reflected or both the transmitted and reflected radiation is measured. Disadvantages of the etching approach as compared to the other approaches are that it is slower and destructive. An advantage of the etching approach as compared to the other approaches is that it has superior resolution and does not necessarily require an inversion algorithm (or can be used as an adjustment and validation tool for existing inversion algorithms).

The measurement system configuration can include that as shown in FIG. 2B or as described in detail for the above embodiments. A difference in this embodiment is that the measurement as done only once in the above embodiments is done, the sample etching procedure is executed, and then the terahertz measurement is repeated. This cycle between etch and terahertz measurement is repeated n times. The search algorithm therefore is given the input of n spectra that is to be matched to a doping profile to be constructed by the algorithm. The model in the algorithm takes into account the first spectrum transmitted through (and/or reflected from) the whole doping profile. The second spectrum transmitted through (and/or reflected from) the whole doping profile minus the first etched layer (for example 10 nm). The third spectrum transmitted through (and/or reflected from) the whole doping profile minus the first two etched layers (for example 2×10 nm=20 nm). The search algorithm therefore constructs a doping profile for which the transmitted spectra though it all, and n ever smaller sub-regions of the doping profile, match the n measured spectra. An error metric is used that measures the collective error between the simulated n spectra and the measured n spectra until a match is found below the prescribed tolerance.

It can be seen that at the cost of being destructive and slower this embodiment potentially has significantly higher resolution (more data is collected) and also more dynamic range (lower doped regions can be relatively obscured by higher doped regions that absorb most of the terahertz probe pulse radiation—as the higher doped region typically closest to the surface is etched away the lower doped regions deeper into the wafer can be resolved more accurately).

An embodiment includes the non-destructive transmission and/or reflection mode measurement with a standard of known doping profile from one generator and one or two detectors. This approach can utilize any coherent sufficiently broadband source (typically pulsed THz-TDS or CW photo-mixing) that can simultaneously measure the phase and amplitude (real and imaginary refractive index) of the material to be analyzed. The phase and amplitude of terahertz radiation of different frequencies is focused on the sample and a doped reference wafer with known doping profile (a 'standard') and either just the transmitted or reflected or both the transmitted and reflected radiation is measured either simultaneously or successively. The doping profile is reconstructed from this data by using the materials library and algorithm to both detect a process deviation and map out the shape of the deviation, or with an algorithm without the need for the materials library to just detect process deviation to only detect the presence of a deviation without the ability to map the precise shape of the deviation between the sample doping profile and the standard (typically desired) doping profile. Using a known doped standard with profile closer to the samples to be analyzed or monitored increases the resolution by which deviation from a desired doping profile can be detected. This implementation will be optimal in industrial quality control and process control applications.

The measurement system configuration can be that as shown in FIG. 2B or described in detail for the above embodiments. The difference in this embodiment is that instead of using an undoped wafer as the reference measurement a 'standard' doped wafer with a known or desirable doping profile is used. If this is done the technique is measuring not the doping profile (relative to no doping) but instead is measuring only the difference or deviation between the standard profile and the sample profile. This approach is most powerful in detecting, monitoring and characterizing process deviations if the measurement configuration in FIG. 2b can be such that the terahertz beam alternates between transmitting through (or reflecting from) the standard and the sample wafer at some known frequency slower than the terahertz pulse frequency. For example, if the laser and terahertz pulse frequency is a typical value like 80 MHz then configuring the system to switch between sample and standard at 1 kHz would be good—that is 80,000 pulses will go through the standard wafer, then 80,000 pulses will go through the standard wafer, then 80,000 pulses will go through the standard wafer etc. back & forth. The advantage of this scheme is that locking detection can be used to very accurately measure (or zoom in) only on the deviation between the sample and the standard.

This embodiment will provide optimal performance in a manufacturing process where the goal of the metrology is to monitor and keep on specification the doping profile in wafers for example micro-electronics, power electronic etc. The ability of the method and system described here to both detect very accurately any deviation between the standard and the sample but moreover also describe the exact shape of the deviation (which is in the present embodiment the equivalent to mapping the shape of the doping profile which is achieved in the previous embodiments) enable intelligent process control. By knowing the precise nature of a deviation one can intelligently adjust process parameters to precisely steer the process back into compliance.

Figure 3:
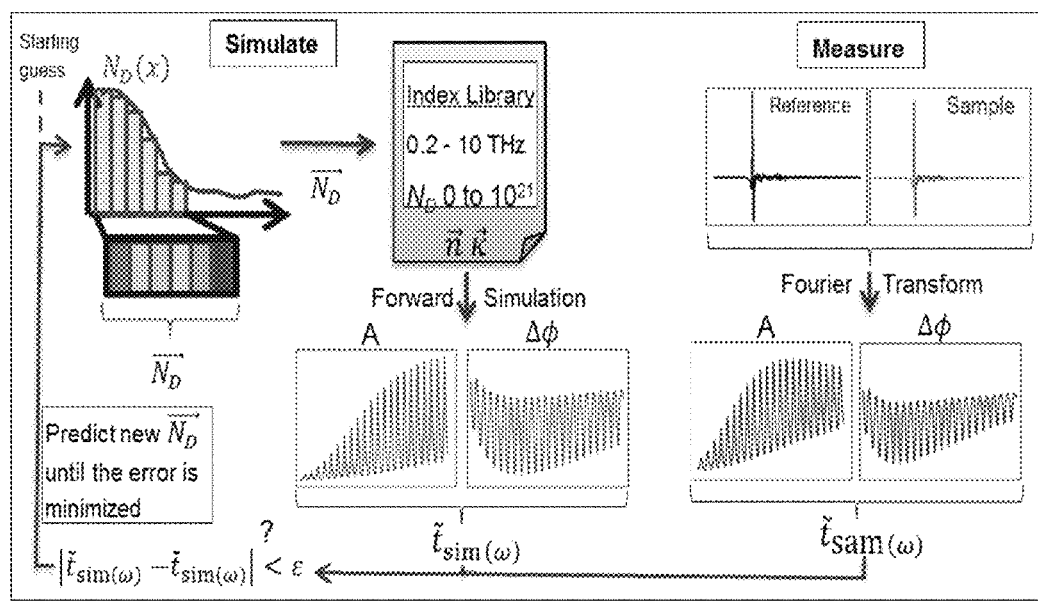
FIG. 3 is a schematic illustrating a methodology of the algorithm and materials index library in accordance with an embodiment of the present invention.

In addition to the hardware and the materials library a mathematical inverse algorithm is used, see FIG. 3. An objective of the algorithm is to take the raw terahertz data obtained in any of the embodiments of the system described above and based on that data construct a reliable estimate of the depth profile of doping below the surface into the wafer. The algorithm constructs this estimate with an iterative search process that is designed to identify or construct the unique profile that will produce a transmitted amplitude and phase spectrum of terahertz light that corresponds exactly to the one measured for the actual real measured wafer. The algorithm takes into account the thickness of the wafer, the absorption and velocity of terahertz light of all frequencies within the doping profile and substrate of the wafer, the reflection of terahertz light of all frequencies from the front and back surface of the wafer, and all internal reflections of terahertz light of all frequencies within the wafer and the doping profile. An embodiment of a methodology of this algorithm and components that together can accomplish this task is illustrated in the schematic in FIG. 3. An illustration of profile mapping with this system and an illustration of an implementation of an algorithm as described is shown below.

The working principles of the algorithm can be described in reference to the diagram in FIG. 3 and the functioning of the algorithm in terms of steps that constitute tan embodiment of the mapping method of doping profile measurement. Step 1, Sample measurement: A measurement is made of a broadband pulse of terahertz light transmitted through the wafer with the doping profile to be mapped. Other embodiments include a reflected, or transmitted and reflected pulses, or multiple pulses in the 'destructive'/etching embodiment. Step 2, Reference measurement: A measurement is made of a broadband pulse of terahertz light transmitted through a reference wafer identical in thickness and composition than the doped wafer or an undoped region of the same wafer. Other embodiments include a reflected pulse or a transmitted pulse or both. Step 3, A/D conversion: Both these measurements are digitized (for example by an A/D converter) and sent to a computer (i.e., fed to the 'algorithm'). Step 4, Numerical Fourier transformation: The Fourier transform of both these pulses are taken. Step 5, Computing $\tilde{t}_{sam}(\omega)$: The complex transmission or reflection coefficient is computed for every terahertz frequency (by dividing the sample transmission coefficient with the reference coefficient at every frequency). This provides, for every frequency ($\omega$), $\tilde{t}_{sam}(\omega)$ as shown in FIG. 3. The blue plot shows the amplitude and phase of $\tilde{t}_{sam}(\omega)$ as a function of frequency—essentially the measure of the transmitted intensity and speed of various frequencies or wavelengths of terahertz light though the diode. Step 6, Providing or generating an initial guess: as shown in the top left of the diagram. To get the algorithm started we feed it a first guess of what we think the diode (doping profile) likely looks like.

There are many options for coming up with this guess. Three possibilities we have used with success are: i) Use a doping profile measured previously by SIMS or mapping of a roughly similar wafer (i.e., one that manufactured under nominally comparable conditions), ii) Generate a theoretically predicted doping profile using a standard semiconductor simulation tool, for example SILVACO, or iii) use a model for the given type (for example diffusion or ion implantation) of a doping profile and choose likely parameters in the model. An example is the 4 parameter RFD model predicting reasonably well the general shape of doping profiles resulting from n-type diffusion processes in silicon (Wirbeleit 2009, Diffusion Fundamentals, 9: p. 5.1-5.7) which is hereby incorporated by reference in its entirety. Step 7, Discretizing the "guess" profile: The algorithm then starts its iterative "search" procedure by taking the "first guess" profile provided as described in step 6 and subdividing or discretizing this profile into an arbitrary number (n) of "slices" or nodes. The larger the number of slices (and the narrower their width) the more accurate the final result. The trade-off is the computational time of the "search". The algorithm can be written so as to make the slices smaller (the node more) until the final solution does not depend on the number of nodes more than a certain tolerable error. Step 8, Simulation of complex transmission: The algorithm then simulates, one by one for every frequency of terahertz light in the real measurement the transmission, reflection and absorption of that frequency through every slice of the discretized profile. The algorithm computes the total complex transmission (amplitude and phase) through all n slices and the wafer substrate for every frequency ($\omega$). The most accurate way to do this is to apply the transmission matrix method (see for example Fowles, Introduction to Modern Optics, which is hereby incorporated by reference in its entirety) to the composite matrix consisting of the n slices and the substrate successively for every frequency ($\omega$). Since the slices are very thin all or "infinite" internal reflections within the slices are included in the simulation. Step 9, Reading from the materials library: Step 9 is a sub-procedure for step 8. To calculate the transmission through any individual slice, and hence the composite of slices (or whole doping profile) the algorithm uses the complex refractive index within every slice. Hence, the algorithm looks up what the real and imaginary value of the terahertz refractive index will be at the doping density specified (by the guess profile) in the center of the slice for the frequency ($\omega$) it is calculating in any given computational step. The algorithm does this by calling up the "materials library". Specifically, the materials library can be a set of matrices (or spreadsheets) listing values of the real and imaginary refractive index at various frequencies (for example, 0.1 THz, 0.11 THz, 0.12 THz, etc. up to 10 THz) spanning the frequency range in the physical measurement. There is a set of matrices (or spreadsheets) providing information at sufficiently many dopant densities spanning the doping density range on the measured diode doping profile. For a typical silicon solar cell one starts such a matrix at the substrate doping density, for example $5 \times 10^{16}$ $cm^{-3}$ and then for example also at $1 \times 10^{17}$ $cm^{-3}$, $5 \times 10^{17}$ $cm^{-3}$, $1 \times 10^{18}$ $cm^{-3}$, $5 \times 10^{18}$ $cm^{-3}$ . . . $5 \times 10^{20}$ $cm^{-3}$. The algorithm therefore has a subroutine that can identify the correct matrices below and above the doping density specified in the slice and accurately interpolate to the real and imaginary refractive index values of doped silicon at the doping density in the slice (at frequency ($\omega$)). Step 10, Comparison and search metrics: Hence, one by one for every frequency ($\omega$), the subroutine can simulate the complex transmission coefficient, $\tilde{t}_{sim}(\omega)$ in FIG. 3. This simulation essentially computes the amplitude and phase of every terahertz frequency (or wavelength) that would exit a wafer with the doping profile exactly as specified with the initial guess. For example, if the initial guess were exactly the same as the actual doping profile in the actual doped wafer then the simulated transmission (red plot in FIG. 3) would agree closely with the measured complex transmission (blue plot in FIG. 3). If this were the case, then the algorithm immediately has found a match, it would report the initial guess as the measured or predicted profile and be done. However, in reality of course this virtually never happens. Due to inevitable process deviation virtually all doping profiles are somewhat unique. Hence, typically the algorithm finds differences between the simulated and the measured complex transmission spectrum (red and blue plots in the illustration). The algorithm quantifies the difference through any standard or suitable error metric. An example would be the sum of squares of the difference at a sample of frequencies $\omega_i$ or the sum of the absolute value of differences. Certain frequencies (where measurement is found more reliable or significant in a given application) can be weighted more heavily than others in the error metric. So, typically the algorithm finds deviation between the measured (blue) complex transmission spectrum and the simulated (red) transmission spectrum that is larger than the tolerance or specification that would signify an acceptable match. Step 11, Iteration, search strategy and termination: Whenever the algorithm determines that the mismatch between the simulated (red) and measured (blue) transmission spectra is larger than the required tolerance or specification the algorithm revisits the initial guess, or guess profile used in the prior or all prior iterations. The next task of the algorithm is to modify the initial guess and re-simulate by repeating steps 8 and 9. It will thus calculate a new simulated (red) profile to be compared with the measured (blue) profile as in step 10. As before, if the difference as calculated by the error metric falls below the acceptable tolerance the algorithm is done and the 'successful' (final "guess") doping profile is provided as the measured or predicted profile. If the error metric again is above the acceptable tolerance the initial guess profile is modified again and steps 8 to 10 repeated. The search algorithm thus repeatedly modifies, simulates and compares the profile until an acceptable match is found. A suitable algorithm is one that implements a search strategy that can reliably converge to a matching profile. Such search strategies of course occupy a large subject area within the field of numerical analysis and digital computing and we have identified several search strategies that work, some more robust but computationally expensive (for example the bisection method), and others (for example the Levenberg-Marquardt) faster but less robust. A perhaps more important aspect to heed than what is the specific search strategy used is to realize that imposing physically relevant constraints on the algorithm is used to ensure the uniqueness of the solution and convergence to the correct physical solution (that correspond to the real doping profile in the actual measured wafer) as opposed to a hypothetical mathematical profile that would yield the same transmission spectrum but does not exist in reality. The more important of these criteria are: i) Continuity of the profile, ii) Realistic constraints regarding the steepness of slope of the profile (a refinement or stricter version of i), iii) Specification of monotonicity where relevant, and iv) a specification of minimum and maximum physically possible doping concentrations. In a unique or esoteric application where any of i) to iii) are not guaranteed for the measured profile the criterion that does not apply should of course be replaced by a relevant criterion or constraint that does apply to the specific application. Step 12, Providing the solution: Whenever the algorithm finds a doping profile for which the simulated complex transmission match the measured complex transmission to within the specification set for the error metric then the algorithm provides the user with the final matching profile and terminates. The measured terahertz data as input, illustrates how to achieve the project object.

An embodiment of a flow diagram of the algorithm that solves the inverse problem of mapping unknown doping profiles is shown in FIG. 3. The algorithm inputs are measured amplitude and phase data and it also uses a real and imaginary materials index library. Shown is a schematic of an algorithm capable of non-destructive doping profile measurement using THz-TDS or any CW THz technique. Note that the algorithm uses two inputs: 1) A measured THz spectrum of the doped sample in transmission and/or reflection mode. 2) A simulated or measured "materials index library" containing the complex refractive index in the terahertz region across the doping levels in the sample. This disclosure describes a method for measure and generating such a THz index library in addition to disclosing the concept and methodology for profile mapping using measured terahertz spectra. (i.e., this disclosure covers the algorithms, software and hardware configurations implementing this method). A schematic (FIG. 3) of an algorithm, that maps out unknown doping profiles with measured terahertz data as input, illustrates how to achieve the project object.

A materials library for the type of material and dopant/chemical profile to be mapped is generated. The information used in the materials library is the frequency dependent complex refractive index in the terahertz region (the part of the spectrum to be used by the measurement apparatus) of the sample material at a set of doping densities spanning the doping range over which the profile is mapped including the highest doping density in the samples to be analyzed. This materials library can be generated by fabricating and measuring the terahertz spectra (real and imaginary refractive index) of a set of thin film samples with uniform ("flat") doping profiles on a suitable terahertz "transparent" substrates (high resistivity silicon or quartz or suitable polymers etc.), see FIG. 4 below. Example 1 below shows how this was successfully done for the case of phosphorous doped silicon. The measurements of the terahertz complex refractive index done this way is the first known measurement of these properties for doping densities $>10^{17}$ atoms/cm$^3$.

Figure 4:
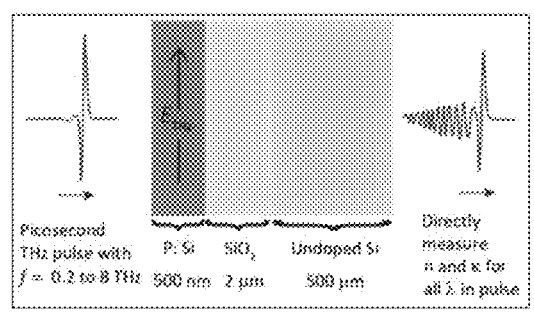
FIG. 4 is a schematic illustrating a method for experimentally generating a materials index library in accordance with an embodiment of the present invention.

FIG. 4 shows an illustration of a method for experimentally generating the materials library. A uniformly doped layer is generated at a fixed doping level to be measured. The thickness of this layer is important. It should be thin enough to allow sufficient terahertz radiation to allow measurement yet thick enough to have bulk conductivity. In highly doped silicon this thickness is approximately 300 to 500 nm. As the doping level is decreased the thickness should be increased. The remainder of the measurement sample structure includes a silicon oxide buffer layer and an undoped high resistivity silicon substrate. By using a technique like THz-TDS one can then measure the complex refractive index in the doped layer at all relevant frequencies. Similar test samples are fabricated at a set of doping densities that span the doping range in the diodes or junctions to be mapped. With sufficiently many doping levels measured one can interpolate between them to obtain the complex refractive index at any doping level in the material system, for example, phosphorous doped silicon as illustrated above.

Example 1

Constructing the Materials Library for Phosphorous Doped Silicon (Si:P) at Room Temperature This example demonstrates a method to experimentally generate a materials library for phosphorous doped silicon. A very accurate experimentally measured materials library can ensure the fidelity of the mapping method as opposed to using a theoretical estimate of the information in the library which almost never is reliable and accurate across the entire dopant range. Using the following method we measured the terahertz refractive index of doped silicon from 0.2 THz-8 THz across all doping levels physically achievable ($10^{15}$ cm$^{-3}$ to $10^{21}$ cm$^{-3}$) at room temperature. Prior to our measurement and demonstration of our method no direct complex refractive index measurements have been demonstrated higher than $10^{17}$ cm$^{-3}$ in doped silicon, that is, the terahertz refractive index at most of the practical silicon device levels have never be measure before. (For reference, the diodes in computer transistors and commercial solar cells have doping levels that go well over $10^{20}$ cm$^{-3}$.) Our method for measuring the refractive index or materials library starts by making use of silicon on insulator (SOI) wafers to fabricate samples with flat doping profiles (uniform doping) to measure and build up the refractive index materials library. An example used successfully is high quality single crystal silicon on insulator (SOI) wafers with the SOI structure being nominally 500 nm intrinsic top Si/3 μm SiO2/500 μm Si substrate. Such wafers are for example fabricated by Soitec SOI with Smart Cut™ technology to transfer and bond a thin layer of high quality single crystalline silicon from a donor substrate to a SOI stack. This approach provides high quality single crystal silicon at submicron thickness without strain and with minimal damage. To fabricate the sample sets doping levels>$10^{17}$ atoms/cm$^3$ the following cleanroom fabrication process was used:

1) ~17 nm sacrificial dry $SiO_2$ was grown on the top Si in a dedicated Bruce tube furnace, 2) Phosphorous ion implantation was done with a Varian 350D Ion Implanter (30 keV implantation energy with dosage adjusted to achieve the various doping levels), 3) Dopant activation and drive-in was achieved by annealing at 1000° C. for 12 hours in a dedicated Bruce tube furnace, 4) HF chemical etching was used to remove the sacrificial oxide.

The flatness of the final doping profile in the top silicon layer can and should be verified with SIMS.

For samples doped at lower (<$10^{17}$ atoms/cm$^3$) doping densities one can simply use high quality single crystal uniformly doped wafers (typically ~200 μm to ~1000 μm) purchased from commercial vendors, characterized and used as is.

Example 2

Measuring the Doping Profile in a Wafer Using the Mapping Method

Figure 5:
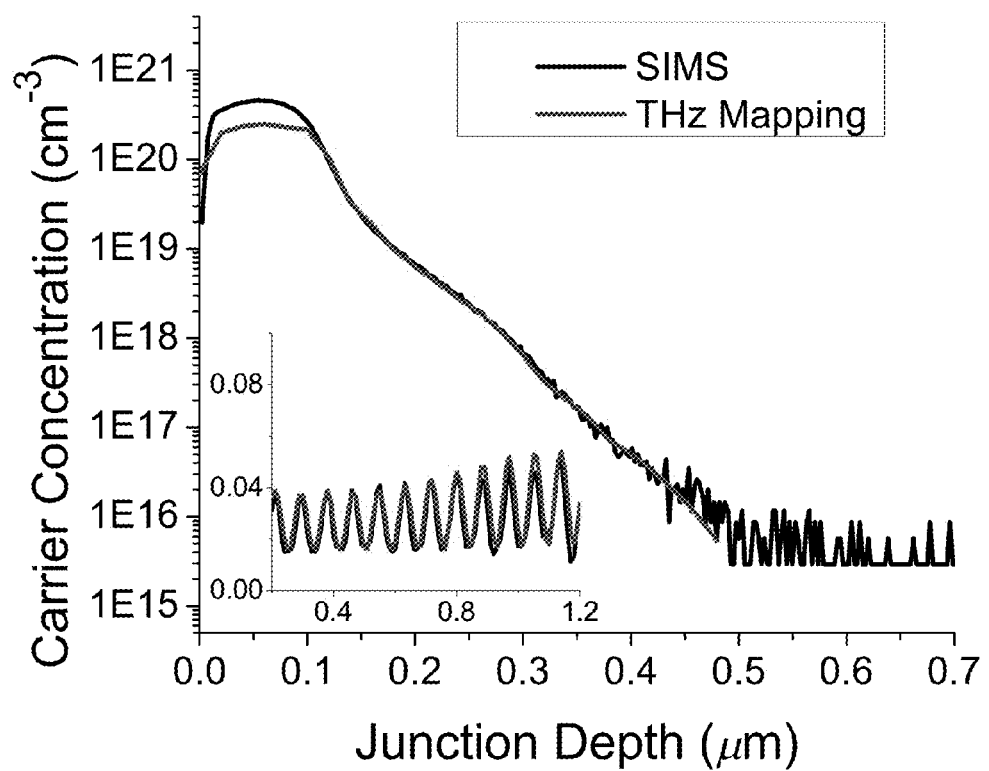
FIG. 5 is a terahertz amplitude transmission spectrum of the doping profile of a phosphorous doped silicon wafer as measured by SIMS and the mapping in accordance with an embodiment of the present invention.

FIG. 5 shows the doping profile of phosphorous doped silicon wafer as measured by SIMS (black) and the present method (red). The inset shows the terahertz amplitude transmission spectrum. It has frequency in THz on the x-axis and electric field amplitude on the y-axis. The black spectrum is the one physically measured with the mapping system (equivalent to the blue curve in FIG. 3) i.e., the Fourier transform of the 'raw data'. The red spectrum is the simulated spectrum (equivalent to the final red spectrum in FIG. 3). Hence, the red spectrum shown in the inset is the transmission spectrum the algorithm obtained by simulating the terahertz transmission of all relevant frequencies through the final profile the search algorithm converged to. The final profile the search algorithm converged to (i.e., the mapping solution) is the red profile provided in the main plot.

Shown in FIG. 5 is a doping profile of P doped Si by ion implantation followed by thermal drive-in. The black curve is measured with SIMS after the non-destructive mapping measurement was completed (red). As can be seen the agreement between the non-destructive and rapid mapping result and the SIMS result is remarkably close from 100 nm to 400 nm below the surface. Over the first 100 nm the chemical dopant density as measured by SIMS exceeds $3\times10^{20}$ cm$^{-3}$ and hence approach the known solubility limit of P atoms in Si. As a result there is likely incomplete activation of the dopant atoms—that is some P atoms are not in substitutional side but instead is interstitial or in P clusters and hence do not contribute free electrons to the conduction band of silicon. Since SIMS merely analyze the concentration of P atoms when the sample is etched away by an ion beam it cannot distinguish between P atoms coming from active and non-active sides. The present mapping on the other hand measures the number of free electrons or free electron density through the interaction of terahertz light with the free electron plasma. Hence, the mapping profile maps the free electron distribution and hence the distribution of activated dopants, which at the high doping end is less than 100% of the chemical dopant atoms present, as can be seen clearly in FIG. 5. The next example illustrates that for diodes and doping profiles where the maximum doping density does not approach the solid solubility limit the mapping measured profile and the SIMS measured profile agrees more closely throughout since the active and chemical doping density then is virtually the same provided the activation processing step was successful. The latter condition, namely whether the activation step in semiconductor manufacturing was successful, is something that only the present mapping can test and verify and SIMS cannot possibly do.

Example 3

Measuring the Doping Profile in a Wafer Using the Mapping Method of the Present Invention This example shows the doping profile obtained in P doped silicon using ion implantation and thermal drive-in conditions as specified. Compared to Example 2 the final peak doping density is lower. As a result the mapping measured profiles and the SIMS measured profiles agree more closely. Also shown in this example is the initial doping profile "guess" used by the mapping algorithm in this specific case. Hence, for each of the two wafers shown the red curve was specified as the initial guess (obtained through a Silvaco simulation). The first round simulation by the mapping algorithm obtained the red transmission spectrum shown. Note that in both cases the red spectrum does not match the black spectrum. The black spectrum is the raw transmission spectrum (amplitude) measured by the mapping system.

Figures 6A, 6B, 6C, 6D:
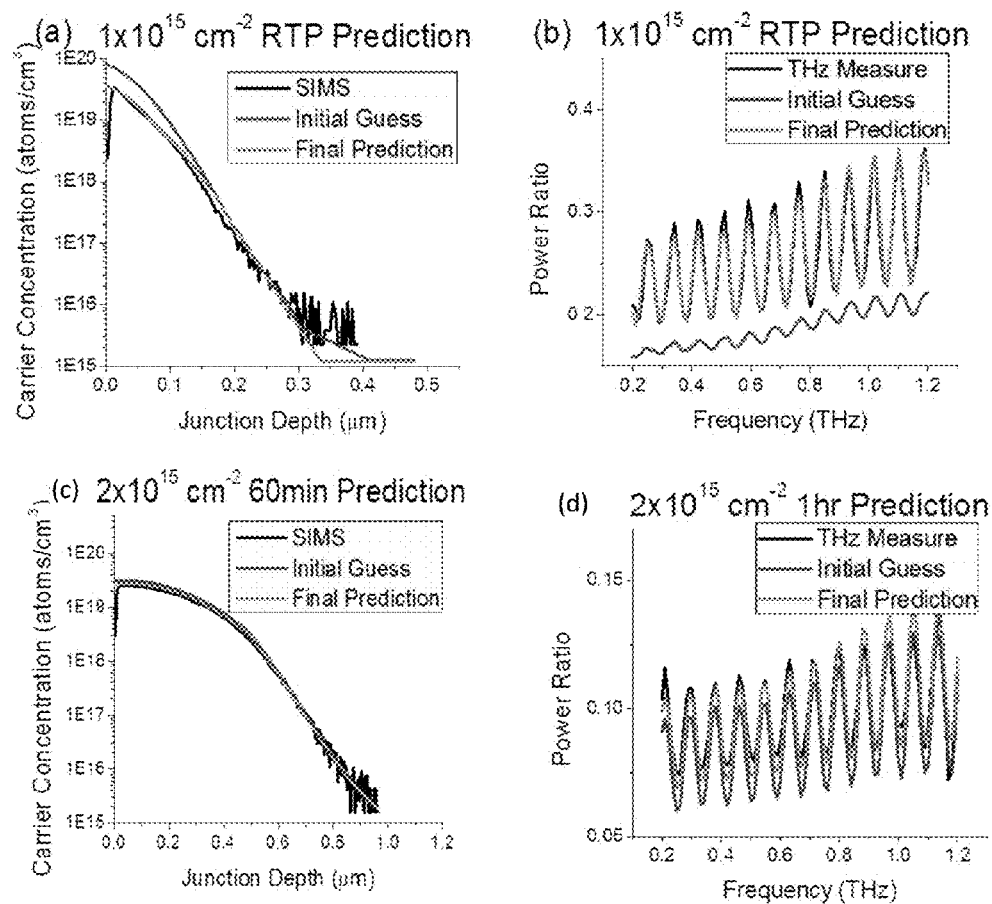
FIG. 6A is doping profile of a Si:P wafer fabricated using ion implantation, 6B shows the measured terahertz transmission spectrum for each wafer, 6C is doping profile of a Si:P wafer fabricated using ion implantation, and 6D shows the measured terahertz transmission spectrum for each wafer.

FIG. 6 shows two Si:P doping profiles (a) and (c) fabricated using ion implantation with the specified dosages and drive-in conditions. While, (b) and (d) show the measured terahertz transmission spectrum for each wafer (black), the spectrum simulated based on the initial guess (red) and the spectrum simulated based on the final doping profile the mapping algorithm converged to (green).

Hence, the fact that the black and red spectra do not match show that the initial guess profile (provided in this case by a SILVACO simulation) is not correct which is typically the case. The next step in the mapping method is then for the algorithm to execute the search routine with the aid of the materials library. The final output of the algorithm, that is the final mapping prediction or measurement of the doping profile is the green doping profile. Also shown is the corresponding spectrum simulated by the mapping algorithm. Although the match between the final mapping simulated spectrum and the measured spectrum is not perfect it is close enough to be below the error metric specification.

Note that in both these examples the maximum doping density is well below the solid solubility limit in Si:P and as a result the agreement between the SIMS measured profile and the mapping measured profile is good.

What is claimed:

1. A system for determining a doping profile of a sample comprising:
   a generator of terahertz light of multiple frequencies;
   a first detector of terahertz light of multiple frequencies, wherein the generator and first detector are configured to operate in a transmission or reflection mode with respect to independently exposing both a sample of unknown doping profile and an undoped reference sample to terahertz frequency radiation traveling through the unknown sample and through the reference sample and detecting a measured spectra of terahertz frequency for each of the unknown sample and the reference sample;
   a materials refractive index library comprising a database comprising multiple doping concentrations of a dopant for a base material and at each of the multiple doping concentrations a refractive index and absorption coefficient at each of different wavelengths; and
   a processor comprising an inverse algorithm that can match simulated spectra using a trial doping profile and the materials library with the measured spectra from the sample, and map out or measure an activated doping profile into, or a free carrier distribution into, the interior of the sample.

2. The system of claim 1, wherein the generator comprises pulsed THz-TDS or CW photo-mixing.

3. The system of claim 1, wherein the doping profile is obtained non-destructively with respect to the sample.

4. The system of claim 1, wherein the sample comprises a diode, coating, thin film, or wafer.

5. The system of claim 1, wherein the measured spectra comprises at least one of phase and amplitude of terahertz radiation of different frequencies that is transmitted through or reflected off the sample and the undoped reference sample.

6. The system of claim 1, further comprising a second detector of terahertz light of multiple frequencies, wherein the generator, first detector and second detector are configured to operate in a transmission and reflection mode with respect to the sample and undoped reference sample.

7. The system of claim 6, wherein the transmission and reflection mode are used in a simultaneous or successive fashion together with the materials refractive index library and the inverse algorithm to map out or measure the doping profile or chemical depth profile of the sample.

8. The system of claim 1, further comprising a material removal or inactivation process capable of removing a layer of the sample after each measurement step to map out or measure the doping profile or chemical depth profile of the sample.

9. The system of claim 8, wherein the material removal or inactivation process comprises plasma treatment, chemical treatment, thermal treatment, exposure to radiation of any kind, etching, polishing, ion milling, sputtering or anodization.

10. The system of claim 6, further comprising a material removal or inactivation process capable of removing a layer of the sample after each measurement step to map out or measure the doping profile or chemical depth profile of the sample.

11. The system of claim 10, wherein the material removal or inactivation process comprises plasma treatment, chemical treatment, thermal treatment, exposure to radiation of any kind, etching, polishing, ion milling, sputtering or anodization.

12. A method for determining a doping profile of a sample comprising:
    providing a generator of terahertz light of multiple frequencies;
    providing a first detector of terahertz light of multiple frequencies, wherein the generator and first detector are configured to operate in a transmission or reflection mode;
    exposing both a sample of unknown doping profile and an undoped reference sample independently to the terahertz frequency radiation traveling through the unknown sample and through the reference sample and detecting a measured spectra of terahertz frequency for each of the unknown sample and the reference sample;
    providing a materials refractive index library comprising a database comprising multiple doping concentrations of a dopant for a base material and at each of the multiple doping concentrations a refractive index and absorption coefficient at each of different wavelengths;
    providing a processor comprising an inverse algorithm; and
    matching simulated spectra using a trial doping profile and the materials library with the measured spectra from the sample, to map out or measure the doping profile or chemical depth profile into the interior of the sample.

13. The method of claim 12, wherein the generator comprises pulsed THz-TDS or CW photo-mixing.

14. The method of claim 12, wherein the doping profile is obtained non-destructively with respect to the sample.

15. The method of claim 12, wherein the sample comprises a diode, coating, thin film, or wafer.

16. The method of claim 12, wherein the measured spectra comprises at least one of phase and amplitude of terahertz radiation of different frequencies that is transmitted through or reflected off the sample and the doped reference sample.

17. The method of claim 12, further comprising providing a second detector of terahertz light of multiple frequencies, wherein the generator, first detector and second detector are configured to operate in a transmission and reflection mode with respect to the sample and doped reference sample.

18. The method of claim 17, wherein the transmission and reflection mode are used in a simultaneous or successive fashion together with the materials refractive index library to measure or map out the doping profile or chemical depth profile of the sample.

19. A system for determining a doping profile of a sample comprising:
    a generator of terahertz light of multiple frequencies;

a first detector of terahertz light of multiple frequencies, wherein the generator and first detector are configured to operate in a transmission or reflection mode, or a first and second detector of terahertz light of multiple frequencies, wherein the generator, first detector and second detector are configured to operate in a transmission and reflection mode, with respect to independently exposing both a sample of unknown doping profile and a doped reference sample having a known doping profile to terahertz frequency radiation traveling through the unknown sample and through the reference sample and detecting a measured spectra of terahertz frequency for each of the unknown sample and the reference sample; and a processor comprising an inverse algorithm that can determine a deviation of the doping profile or chemical depth profile into the interior of the sample of unknown doping profile from the doped reference sample of known doping profile.

20. The system of claim 19, wherein the processor further comprises a materials library that, in combination with the inverse algorithm, can determine the deviation of the doping profile or chemical depth profile of the sample of unknown doping profile from the doped reference sample of known doping profile.

21. The method of claim 12, wherein the matching simulated spectra comprises comparing the simulated spectra of the trail doping profile to the measured spectra of the sample to determine a difference in spectra, providing a further trial doping profile that reduces the difference in spectra of the trail doping profile to the measured spectra of the sample until the difference in spectra is acceptable.

* * * * *